(12) United States Patent
Khoshdel et al.

(10) Patent No.: US 9,744,109 B2
(45) Date of Patent: Aug. 29, 2017

(54) EUTECTIC MIXTURES IN PERSONAL CARE COMPOSITIONS

(71) Applicant: Conopco, Inc., Englewood Cliffs, NJ (US)

(72) Inventors: Ezat Khoshdel, Neston (GB); Stephan Georg Schumm, Rotterdam (NL); Yinfang Yao, Shanghai (CN); Qiqing Zhang, Shanghai (CN)

(73) Assignee: Conopco. Inc., Englewood Cliffs, NJ (US)

( * ) Notice: Subject to any disclaimer, the term of this patent is extended or adjusted under 35 U.S.C. 154(b) by 0 days.

(21) Appl. No.: 14/651,676

(22) PCT Filed: Nov. 26, 2013

(86) PCT No.: PCT/EP2013/074696
§ 371 (c)(1),
(2) Date: Jun. 12, 2015

(87) PCT Pub. No.: WO2014/095257
PCT Pub. Date: Jun. 26, 2014

(65) Prior Publication Data
US 2015/0313815 A1 Nov. 5, 2015

(30) Foreign Application Priority Data

Dec. 20, 2012 (WO) ................ PCT/CN2012/087070
Jan. 25, 2013 (EP) .................................... 13152645

(51) Int. Cl.
| | |
|---|---|
| *A61K 8/35* | (2006.01) |
| *A61K 8/37* | (2006.01) |
| *A61Q 17/04* | (2006.01) |
| *A61K 8/67* | (2006.01) |
| *A61K 8/365* | (2006.01) |
| *A61Q 19/00* | (2006.01) |

(52) U.S. Cl.
CPC ................ *A61K 8/35* (2013.01); *A61K 8/365* (2013.01); *A61K 8/37* (2013.01); *A61K 8/675* (2013.01); *A61Q 17/04* (2013.01); *A61Q 19/00* (2013.01); *A61K 2800/10* (2013.01); *A61K 2800/59* (2013.01)

(58) Field of Classification Search
CPC .. A61K 2800/10; A61K 2800/59; A61K 8/35; A61K 8/365; A61K 8/37; A61K 8/675; A61Q 17/04; A61Q 19/00
USPC ......................................................... 424/59
See application file for complete search history.

(56) References Cited

U.S. PATENT DOCUMENTS

| | | | |
|---|---|---|---|
| 5,759,524 A | 6/1998 | Tanner | |
| 6,197,343 B1 | 3/2001 | Minami | |
| 6,306,373 B1 | 10/2001 | Impernate | |
| 6,423,325 B1 | 7/2002 | Alaluf | |
| 6,680,285 B2 | 1/2004 | Abbas | |
| 6,713,051 B2 | 3/2004 | Mayes | |
| 7,781,429 B2 | 8/2010 | Schwarz et al. | |
| 2004/0018954 A1 | 1/2004 | Su | |
| 2004/0028709 A1* | 2/2004 | Dueva ..................... | A61K 8/73 424/401 |
| 2004/0043044 A1 | 3/2004 | Granger | |
| 2004/0044078 A1 | 3/2004 | Kawa | |
| 2005/0013781 A1 | 1/2005 | Dueva-Koganov et al. | |
| 2008/0031835 A1 | 2/2008 | Kawamura et al. | |
| 2009/0317341 A1 | 12/2009 | Madison | |
| 2010/0093682 A1 | 4/2010 | Ishida | |
| 2012/0128744 A1 | 5/2012 | Sorge et al. | |
| 2012/0183480 A1 | 7/2012 | Nagare et al. | |

FOREIGN PATENT DOCUMENTS

| | | |
|---|---|---|
| CN | 1500524 | 6/2004 |
| CN | 101849890 | 10/2010 |
| EP | 0129528 A1 | 12/1984 |
| EP | 2174642 | 4/2010 |
| JP | 09048962 | 2/1997 |
| JP | 200395848 | 4/2003 |
| JP | 2009286739 | 10/2009 |
| JP | 2010138110 | 6/2010 |
| KR | 20090121848 | 11/2009 |
| KR | 20090121848 A * | 11/2009 |
| WO | WO9531961 | 11/1995 |
| WO | WO2006056283 | 6/2006 |
| WO | WO2011095392 | 8/2011 |
| WO | WO2012061991 | 5/2012 |

OTHER PUBLICATIONS

IPRP2 in PCTEP2013074687 dated Feb. 9, 2015.
Search Report in EP13152644 date Jun. 5, 2013.
Search Report in PCTEP2013074687 dated May 27, 2014.
Written Opinion in EP13152644 dated Jun. 5, 2013.
Written Opinion in PCTEP2013074687 dated May 27, 2014.
Co-pending Application: Applicant: Khoshdel et al., U.S. Appl. No. 14/651,674, filed Jun. 15, 2015.
Fialas et al., "A fundamental investigation into the effects of eutectic formation on transmembrane transport", International Journal of Pharmaceutics, Jun. 30, 2010, vol. 393, pp. 68-73.
Marti-Mestres et al., "Stability of UV filters in different vehicles Solvent and Emulsions", Drug Development and Industrial Pharmacy, 1997, vol. 23, No. 7, pp. 647-655.
Benson, "Transdermal Drug Delivery: Penetration Enhancement Techniques", Current Drug Delivery, 2005, vol. 2, No. 1, pp. 23-33.
IPRP2 in PCTEP2013074696, Apr. 1, 2015.
Vallejo et al., "Evaluation of the avobenzone photostability in solvents used in cosmetic formulations", Vitae Revista de la facultad de quimica farmaceutica, Jan. 1, 2011, vol. 18 (1), pp. 63-71.

(Continued)

*Primary Examiner* — Janet Epps-Smith
*Assistant Examiner* — Courtney Brown
(74) *Attorney, Agent, or Firm* — Edward A. Squillante, Jr.

(57) ABSTRACT

The invention relates to active eutectic mixtures of butyl methoxydibenzoylmethane, isopropyl myristate and optionally 12-hydroxystearic acid, personal care products comprising such active eutectic mixtures, a method for preparing such personal care compositions and a method of applying to human skin such personal care compositions.

13 Claims, 3 Drawing Sheets

(56) References Cited

OTHER PUBLICATIONS

Matuo et al., "Eutectic transformation in mixed monolayers of long normal chain fatty acids with 12-hydroxyoctadecanoic acid", Chemistry and Physics of Lipids, Aug. 1, 1981, vol. 29, No. 1, pp. 55-67.
Search Report in EP13152645, Jun. 7, 2013.
Search Report in PCTEP2013074696, May 9, 2014.
Written Opinion in EP13152645, Jun. 7, 2013.
Written Opinion in PCTEP2013074696, Dec. 8, 2014.
Butyl Methoxydibenzoylmethane, Personal Care Products Council, 2015, p. 1.
Gefrierpunktserniedrigung, Wikipedia, 2016, pp. 1-12 (with Translation).
Notice of Opposition EP13796053 (EP2934458), Dec. 22, 2016 (with Translation).
Hirosi Matuo et al., Effects of Molecular Structure on Two-Dimensional Phase Diagram and Thermodynamic Quantities of Mixed Monolayers, Chemistry and Physics of Lipids, 1981, pp. 385-397, vol. 48, No. 4, Elsevier.

\* cited by examiner

EUTECTIC MIXTURES IN PERSONAL CARE COMPOSITIONS

FIELD OF THE INVENTION

The present invention relates to eutectic mixtures of butyl methoxydibenzoylmethane, isopropyl myristate and optionally 12-hydroxystearic acid; and personal care compositions comprising such eutectic mixtures.

BACKGROUND OF THE INVENTION 12-hydroxystearic acid (hereinafter "12-HSA") is reported to have a wide variety of beneficial cosmetic effects on skin. It is a known PPAR-alpha (peroxisome proliferator activated receptors sub-type alpha) activator, skin lightening agent, and a sebum secretion inhibitor. See e.g. Alaluf et al. U.S. Pat. No. 6,423,325, Mayes et al. U.S. Pat. No. 6,713,051, WO2006/056283 (Hindustan Lever), Madison US 2009/0317341, Minami et al. U.S. Pat. No. 6,197,343, Granger et al. US2004/0043044.

As such, cosmetic products containing 12-HSA are highly desirable.

JP 09-048962 describes the use of 12-HSA or its salt as an effective constituent of a solidification inhibitor, to inhibit solidification of a liquid detergent or a liquid cosmetic; all the examples containing a fully neutralized salt of 12-HSA. 12-HSA has traditionally been used as gelling agent e.g. in lipsticks and antiperspirant compositions. See also EP 0129528, U.S. Pat. No. 6,680,285, Abbas et al. U.S. Pat. No. 6,680,285, Tanner et al. U.S. Pat. No. 5,759,524, WO95/31961 (Procter &. Gamble), Kawa et al., US 2004/0044078 (describing the use of 12-HSA to increase viscosity of cosmetic compositions), and JP 2010/138,110.

Unfortunately, 12-HSA is a solid having a melting point of about 72 to 77 degrees Celsius, has no water solubility and limited oil solubility. Salts of 12-HSA are only marginally more water-soluble. Because of the high melting temperature it is difficult to formulate in a personal care composition, often requiring elevated temperatures or solvents. Lowering the 12-HSA melting point or at least have it (partially) available as a non-solid may be desirable as this may e.g. influence the bioavailability or ease of use of 12-HSA or personal care compositions comprising 12-HSA. Another drawback associated with the high melting point of 12-HSA is that it may re-crystallize upon storage after being incorporated in a personal care product in non-solid form like e.g. in a solvent. Such re-crystallization may cause the undesired gellation of such personal care products thereby destroying the texture thereof.

Butyl methoxydibenzoylmethane ("BMDM") is a well-known UV-A organic sunscreen that is used in personal care composition like sunscreen formulations and other skin leave-on compositions to provide protection against the full spectrum of UV-A rays. It is available under the trade name Parsol 1789®. It is a solid having a melting point of about 83 degrees Celsius. As such it may be difficult to formulate in a personal care composition, often requiring elevated temperatures or solvents. BMDM has a finite oil solubility and this characteristic is used to formulate BMDM in for example a sunscreen. As with 12-HSA, BMDM may re-crystallize upon storage after being incorporated in a personal care product in non-solid form like e.g. in a solvent. Such re-crystallization may cause the undesired gellation of such personal care products thereby destroying the texture thereof.

The present inventors have identified a need for alternative methods to incorporate 12-HSA and/or BMDM in personal care products that at least in part do not have one or more of the aforementioned drawbacks.

SUMMARY OF THE INVENTION

The present inventors have found that certain mixtures comprising BMDM and isopropyl myristate ("IPM") optionally also including 12-HSA have a lower melting point than BMDM and 12-HSA itself.

Accordingly, the invention relates to an active eutectic mixture of butyl methoxydibenzoylmethane, isopropyl myristate and optionally 12-hydroxystearic acid.

The invention further relates to a personal care composition comprising
i) the active eutectic mixture according the invention, and
ii) a cosmetically acceptable carrier.

In another aspect the invention relates to a method for preparing the personal care composition according to the invention comprising the step of mixing the preformed active eutectic mixture according to the invention of butyl methoxydibenzoylmethane, isopropyl myristate and if present 12-hydroxystearic acid with part or all of the remaining ingredients of the personal care composition.

The invention also relates to a personal care composition obtainable by the method of the invention.

The invention further relates to a method of applying to human skin the personal care composition according to the present invention.

BRIEF DESCRIPTION OF THE FIGURES

Certain embodiments of the invention will be described with reference to the figures in which.

DETAILED DESCRIPTION OF THE INVENTION

All amounts are by weight of the total composition, unless otherwise specified. Room temperature is defined as a temperature of about 20 degrees Celsius.

Eutectic Mixtures

A eutectic system is a mixture of chemical compounds or elements that has the lowest melting point of any other mixture made up of the same ingredients and wherein the composition of the liquid and the solid that are in equilibrium at this lowest melting temperature are the same. This composition is known as the "eutectic composition" and the corresponding melting temperature as the "eutectic temperature".

The present invention relates to the mixture of two or three components that gives rise to a binary or ternary eutectic composition, i.e. a binary or ternary composition that has a lower melting point than any other composition made of the two or three components.

For the purpose of the present invention an "active eutectic mixture" is defined as any binary or ternary mixture of the two or three components of the present invention that is in the liquid state above a given melting temperature.

The active eutectic mixtures of the invention are mixtures of butyl methoxydibenzoylmethane, isopropyl myristate and (optionally) 12-hydroxystearic acid, wherein the weight ratio of butyl methoxydibenzoylmethane to isopropyl myristate is from 3:7 to 1:15; the concentration of 12-hydroxystearic acid calculated on total weight of the eutectic mixture is from 0 to 6 wt %; and wherein the eutectic mixture has a melting point below 15 degrees Celsius.

The butyl methoxydibenzoylmethane and isopropyl myristate are thus present in a weight ratio from 3:7 to 1:15. Preferably the weight ratio of BMDM to IPM is from 3:7 to 1:10, more preferably from 3:7 to 1:9, and even more preferably from 2:8 to 1:9.

The concentration of 12-hydroxystearic acid calculated on total weight of the eutectic mixture is from 0 to 6 wt %. Preferably the concentration of 12-hydroxystearic acid calculated on total weight of the eutectic mixture is from 0.1 to 6 wt %, more preferably from 0.5 to 6 wt %, even more preferably from 0.5 to 5 wt % and still more preferably from 1 to 4 wt %.

For example a preferred active eutectic mixture of 9.65 wt % BMDM, 86.85 wt % IPM and 3.5 wt % 12-HSA corresponds to 96.5% wt % (BMDM+IPM) in a weight ratio of 1:9 and a concentration of 12-hydroxystearic acid of 3.5 wt % with respect to the total weight of the three components together.

The active eutectic mixture of the invention may be a binary eutectic mixture of BMDM and IPM. In this case 12-HSA is not part of the eutectic mixture. Preferred binary eutectic mixtures have a BMDM to IPM weight ratio of 3:7 to 1:10, like for example 2:8 or 1:9.

Preferred active eutectic mixtures of the invention are ternary eutectic mixtures of BMDM, IPM and 12-HSA. Preferred ternary eutectic mixtures have a BMDM to IPM weight ratio of 3:7 to 1:10 and a concentration of 12-hydroxystearic acid of 0.1 to 6 wt %, like for example a BMDM to IPM weight ratio of 3:7 to 1:10 and a concentration of 12-hydroxystearic acid of 2 wt %; a BMDM to IPM weight ratio of 3:7 to 1:10 and a concentration of 12-hydroxystearic acid of 3.5 wt %; a BMDM to IPM weight ratio of 3:7 to 1:10 and a concentration of 12-hydroxystearic acid of 6 wt %; a BMDM to IPM weight ratio of 2:8 to 1:10 and a concentration of 12-hydroxystearic acid of 2 wt %; a BMDM to IPM weight ratio of 2:8 to 1:10 and a concentration of 12-hydroxystearic acid of 3.5 wt %; a BMDM to IPM weight ratio of 2:8 to 1:10 and a concentration of 12-hydroxystearic acid of 6 wt %; a BMDM to IPM weight ratio of 1:9 and a concentration of 12-hydroxystearic acid of 3.5 wt %.

The melting point of the eutectic mixture according to the invention is below 15 degrees Celsius. Preferably the mixture has a melting point below 12 degrees Celsius, more preferably below 10 degrees Celsius, even more preferably below 9 degrees Celsius, still more preferably below 8 degrees Celsius, even still more preferably below 7 degrees Celsius and more so preferably below 6 degrees Celsius. Preferably the melting point of the eutectic mixture is greater than minus seventy (−70) degrees Celsius.

The amounts of the ingredients in the eutectic mixture of the invention will determine the melting of said mixture and can be suitably determined using well known methods as described in the example section of this specification.

Preferred eutectic mixtures have a BMDM to IPM weight ratio of 3:7 to 1:10; a concentration of 12-hydroxystearic acid from 0.1 to 6 wt %; and a melting point below 10 degrees Celsius. An example of such a preferred eutectic mixture is a eutectic mixture that has a BMDM to IPM weight ratio of 2:8 to 1:9; a concentration of 12-hydroxystearic acid from 1 to 6 wt %; and a melting point below 9 degrees Celsius.

12-HSA

The inventive eutectic mixtures may include 12-HSA. Preferably the inventive eutectic mixtures include 12-HSA. The 12-HSA is used in its acid form as this will form a ternary eutectic mixture with BMDM and IPM. A further advantage is that 12-HSA in its acid form may have a better bioavailability, especially so if part of a eutectic mixture in which it is liquid at human skin temperature (i.e. about 37 degrees Celsius) or room temperature. As with other fatty acids the apparent pKa for 12-HSA is expected to be greater than 8. Preferably, the active eutectic mixtures of the invention have a pH between 3 and 4.

BMDM and IPM

BMDM is a solid at room temperature having a melting point of about 83 degrees Celsius.

We have found that certain mixtures of BMDM and IPM form a binary eutectic mixture. Eutectic compositions have a narrow formulation space. Once a combination of two ingredients has been found to form a eutectic composition there is little to no tolerance for replacing the specific ingredients or adding further ingredients without destroying the eutectic characteristics thereof. It was surprisingly found that a specific combination of BMDM, IPM and 12-hydroxystearic acid forms a ternary eutectic mixture.

The active eutectic mixtures of the present invention can be suitably made using conventional techniques and can be for example made by simply mixing the ingredients in the required amounts by grinding them until a homogenous mixture is obtained.

Personal Care Composition

Personal care compositions of the invention comprise:
i) the active eutectic mixture according the invention, and
ii) a cosmetically acceptable carrier.

The personal care compositions of the invention may comprise up to 60 wt % of the eutectic mixture calculated on total personal care composition, more preferably up to 50 wt %, even more preferably up to 40 wt %, still more preferably up to 30 wt %, still even more preferably up to 20 wt %, and even still more preferably up to 10 wt %. Preferably the personal care composition comprises at least 0.1 wt % of the eutectic mixture calculated on total personal care composition, more preferably at least 0.5 wt %, even more preferably at least 1 wt %, still more preferably at least 3 wt % and even still more preferably at least 5 wt %. Preferred amounts of the eutectic mixture in the personal care composition are from 0.1 to 60 wt %, more preferably from 0.5 to 50 wt %, even more preferably from 1 to 40 wt %, still more preferably from 2 to 30 wt %, still even more preferably from 3 to 20 wt % and optimally from 5 to 15 wt %.

The personal care composition preferably comprises from 0 to 15 wt % of 12-hydroxystearic acid calculated on total personal care composition, more preferably from 0.01 to 12 wt %, still more preferably from 0.1 to 10 wt %, even more preferably from 0.5 to 8 wt % and still more preferably from 1 to 5 wt %. Typical amounts of 12-hydroxystearic acid in the personal care composition according to the invention are from 0.01 to 15 wt %, from 0.1 to 12 wt %, and 0.5 to 10 wt %. The amounts of 12-HSA are not meant to be included within the surfactants amounts herein.

As with other fatty acids the apparent pKa for 12-HSA is expected to be greater than 8. At the pKa, the fatty acid will exist as 50% soap and 50% acid. Therefore, preferably the pH of the personal care compositions is less than about 8, more preferably is in the range of from 3.5 to 8.0, even more preferably is from 5 to 7.8 and still more preferably is from 5.5 to 7.

The personal care composition preferably comprises from 0.1 to 10 wt % of butyl methoxydibenzoylmethane calculated on total personal care composition, more preferably from 0.1 to 8 wt %, still more preferably from 0.1 to 6 wt %, and even more preferably from 0.5 to 4 wt %.

It is to be understood that any one of the components making up the active eutectic mixture in the personal care composition may also be added to the personal care composition in addition to the components present as part of the eutectic mixture. The amount given for the component is the total amount of the same in the personal care composition. Preferably the components of the active eutectic mixture in the personal care composition are only present as part of the active eutectic mixture.

It should be known that commercially acceptable and conventional vehicles may be used acting as diluents, dispersants and/or carriers for the active eutectic mixture of the invention and additives described herein and for any other optional but often preferred additives. Therefore, the cosmetically acceptable carrier suitable for use in this invention may be aqueous-based, anhydrous or an emulsion whereby a water-in-oil or oil-in-water emulsion is generally preferred. If the use of water is desired, water typically makes up the balance of the cosmetic composition, and preferably makes up from 5 to 99 wt %, and most preferably from 40 to 80 wt % by calculated on total personal care composition including all ranges subsumed therein.

In addition to water, organic solvents may be optionally included within the compositions of the present invention. Illustrative and non-limiting examples of the types of organic solvents suitable for use in the present invention include alkanols like ethyl and isopropyl alcohol, mixtures thereof or the like.

Other optional additives suitable for use include ester oils like cetyl myristate, 2-octyldodecyl myristate, avocado oil, almond oil, olive oil, neopentylglycol dicaprate, mixtures thereof or the like. Typically such ester oils assist in emulsifying the personal care composition of this invention, and an effective amount is often used to yield a stable, and most preferably water-in-oil emulsion. Such ester oils may be in addition to isopropyl myristate (IPM) as part of the eutectic mixture of the present invention.

Emollients may also be used, if desired, within the personal care composition of the present invention. Alcohols like 1-hexadecanol (i.e. cetyl alcohol) and phenoxyethanol are often desired as are the emollients generally classified as silicone oils and synthetic esters. Silicone oils suitable for use include cyclic or linear polydimethylsiloxanes containing from 3 to 9, preferably from 4 to 5 silicon atoms. Non-volatile silicone oils useful as an emollient material in the inventive personal care composition described herein include polyalkyl siloxanes, polyalkylaryl siloxanes and polyether siloxane copolymers. The essentially non-volatile polyalkyl siloxanes useful herein include, for example, polydimethylsiloxanes.

The ester emollients that may optionally be used are:
(1) Alkenyl or alkyl esters of fatty acids having 10 to 20 carbon atoms. Examples thereof include isoarachidyl neopentanoate, isononyl isonanonoate, oleyl myristate, oleyl stearate and oleyl oleate.
(2) Ether-esters such as fatty acid esters of ethoxylated fatty alcohols.
(3) Polyhydric alcohol esters. Ethylene glycol mono- and di-fatty acid esters, diethylene glycol mono- and di-fatty acid esters, polyethylene glycol (200-6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty esters, ethoxylated glyceryl mono-stearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters.
(4) Wax esters such as beeswax, spermaceti, stearyl stearate and arachidyl behenate.
(5) Sterols esters, of which cholesterol fatty acid esters are examples.

Emollients, when used, typically make up from 0.1 to 50 wt % on total composition including all ranges subsumed therein.

Fatty acids having from 10 to 30 carbon atoms may also be included as cosmetically acceptable carriers within the composition of the present invention. Illustrative examples of such fatty acids include pelargonic, lauric, myristic, palmitic, stearic, isostearic, oleic, linoleic, arachidic, behenic or erucic acid and mixtures thereof. These fatty acids are in addition to the 12-HSA that is present as part of the active eutectic mixture.

Compounds that are believed to enhance skin penetration, like dimethyl sulfoxide, may also be used as an optional carrier.

Humectants of the polyhydric alcohol type may also be employed in the personal care compositions of this invention. The humectant often aids in increasing the effectiveness of the emollient, reduces scaling, stimulates removal of built-up scale and improves skin feel. Typical polyhydric alcohols include glycerol, polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-butylene glycol, 1,2,6-hexanetriol, ethoxylated glycerol, propoxylated glycerol and mixtures thereof. For best results the humectant is preferably propylene glycol or sodium hyaluronate. The amount of humectant may range anywhere from 0.2 to 25 wt %, and preferably from 0.5 to 15 wt % on total cosmetic composition and including all ranges subsumed therein.

Thickeners may also be utilized as part of the cosmetically acceptable carrier in the personal care compositions of the present invention. Typical thickeners include cross-linked acrylates (e.g. Carbopol 982), hydrophobically-modified acrylates (e.g. Carbopol 1382), cellulosic derivatives and natural gums. Among useful cellulosic derivatives are sodium carboxymethylcellulose, hydroxypropyl methylcellulose, hydroxypropyl cellulose, hydroxyethyl cellulose, ethyl cellulose and hydroxymethyl cellulose. Natural gums suitable for the present invention include guar, xanthan, sclerotium, carrageenan, pectin and combinations of these gums. Amounts of the thickener may range from 0 to 5 wt %, usually from 0.001 to 1 wt %, optimally from 0.01 to 0.5 wt % on total composition.

Collectively, the water, solvents, silicones, esters, fatty acids, humectants and/or thickeners will constitute the cosmetically acceptable carrier in amounts from 1 to 99.9 wt %, preferably from 80 to 99 wt % on total composition.

Surfactants may also be present in cosmetic compositions of the present invention. Total concentration of the surfactant will range from 0 to 40 wt %, and preferably from 0 to 20 wt % optimally from 0 to 5 wt % on total composition. The surfactant may be selected from the group consisting of anionic, nonionic, cationic and amphoteric actives. Particularly preferred nonionic surfactants are those with a C10-C20 fatty alcohol or acid hydrophobe condensed with from 2 to 100 moles of ethylene oxide or propylene oxide per mole of hydrophobe; C2-C10 alkyl phenols condensed with from 2 to 20 moles of alkylene oxide; mono- and di-fatty acid esters of ethylene glycol; fatty acid monoglyceride; sorbitan, mono- and di-C8-C20 fatty acids; block copolymers (ethylene oxide/propylene oxide); and polyoxyethylene sorbitan as well as combinations thereof. Alkyl polyglycosides and saccharide fatty amides (e.g. methyl gluconamides) are also suitable nonionic surfactants.

Preferred anionic surfactants include soap, alkyl ether sulfate and sulfonates, alkyl sulfates and sulfonates, alkylbenzene sulfonates, alkyl and dialkyl sulfosuccinates, C8-C20 acyl isothionates, acyl glutamates, C8-C20 alkyl ether phosphates and combinations thereof.

Perfumes may be used in the cosmetic composition of this invention. Illustrative nonlimiting examples of the types of perfumes that may be used include those comprising terpenes and terpene derivatives like those described in Bauer, K., et al., *Common Fragrance and Flavor Materials*, VCH Publishers (1990). Illustrative yet non-limiting examples of the types of fragrances that may be used in this invention include myrcene, dihydromyrenol, citral, tagetone, cis-geranic acid, citronellic acid, or cis-geranic acid nitrile, mixtures thereof or the like. Preferably, the amount of fragrance employed in the cosmetic composition of this invention is in the range from 0 to 10 wt %, more preferably 0.00001 to 5 wt %, most preferably 0.0001 to 2 wt %.

Various types of optional additional active ingredients may be used in the cosmetic compositions of the present invention. Actives are defined as skin benefit agents other than emollients and other than ingredients that merely improve the physical characteristics of the composition. Although not limited to this category, general examples include talcs and silicas, as well as alpha-hydroxy acids, beta-hydroxy acids, peroxides, zinc salts and sunscreens.

Beta-hydroxy acids include salicylic acid, for example. Zinc pyrithione is an example of the zinc salts useful in the personal care composition of the present invention.

Preferably the personal care composition of the invention comprises additional sunscreen agents, i.e. in addition to BMDM, like for example other UV-B sunscreen agents to protect against the entire gamut of UV rays. Preferably selected from organic UVA sunscreen, organic UVB sunscreen, inorganic sunscreen and combinations thereof. Particularly preferred are such materials as ethylhexyl p-methoxycinnamate, available as Parsol MCX®, and benzophenone-3 also known as Oxybenzone. Inorganic sunscreen actives may be employed such as microfine (1 to 100 nm) titanium dioxide and zinc oxide. Total amounts of the sunscreen agents present, including BMDM, may generally range from 0.1 to 30 wt %, preferably from 2 to 20 wt %, optimally from 4 to 10 wt % on total composition.

Many personal care compositions, especially those containing water, should be protected against the growth of potentially harmful microorganisms. Anti-microbial compounds, such as triclosan, and preservatives are typically necessary. Suitable preservatives include alkyl esters of p-hydroxybenzoic acid, hydantoin derivatives, propionate salts and a variety of quaternary ammonium compounds. Particularly preferred preservatives of this invention are methyl paraben, propyl paraben, phenoxyethanol and benzyl alcohol. Preservatives will usually be employed in amounts ranging from 0.1 to 2 wt % on total composition.

Preferably the personal care composition of the invention comprises a vitamin. Illustrative vitamins are Vitamin A (retinol), Vitamin $B_2$, Vitamin $B_3$ (niacinamide), Vitamin $B_6$, Vitamin C, Vitamin E, Folic Acid and Biotin. Derivatives of the vitamins may also be employed. For instance, Vitamin C derivatives include ascorbyl tetraisopalmitate, magnesium ascorbyl phosphate and ascorbyl glycoside. Derivatives of Vitamin E include tocopheryl acetate, tocopheryl palmitate and tocopheryl linoleate. DL-panthenol and derivatives may also be employed. Total amount of vitamins when present in compositions according to the present invention may range from 0.001 to 10 wt %, preferably from 0.01 to 1 wt %, optimally from 0.1 to 0.5 wt % on total composition. Preferably the personal care composition of the invention comprises a vitamin, wherein the vitamin comprises niacinamide.

Personal care compositions of the present invention are preferably selected from leave-on skin lotions and creams, shampoos, hair conditioners, shower gels, toilette bars, antiperspirants, deodorants, shave creams, lipsticks, foundations and sunscreen lotions.

The personal care composition of the invention is preferably a sunscreen or a leave-on skin lotion or cream.

Personal care compositions of the present invention may be in any form. These forms may include lotions, creams, roll-on formulations, sticks, mousses, aerosol and non-aerosol sprays and fabric (e.g. nonwoven textile)-applied formulations.

The personal care compositions of the present invention preferably are non-solid. Essentially, the "non-solidness" of the composition means that the viscosity of the compositions, e.g. as measured using a Brookfield DV-I+viscometer (20 RPM, RV6, 30 seconds)], in general is in the range of from 1 Pas to 500 Pas, preferably from 1 Pas to 200 Pas, more preferably from 2 Pas to 100 Pas, most preferably from 3 Pas to 50 Pas at 20 degrees Celsius.

Even though the skin benefits of 12-HSA may also be delivered as part of a rinse off personal care composition, preferred compositions of the invention are leave-on compositions (i.e. personal care compositions that are meant to be left on after application by the consumer to the appropriate area of the human body like skin and/or hair). Preferred compositions of the present invention are intended to be applied to remain on the skin. These leave-on compositions are to be distinguished from compositions which are applied to the skin and subsequently removed either by washing, rinsing, wiping, or the like either after or during the application of the product. Surfactants typically used for rinse-off compositions have physico-chemical properties giving them the ability to generate foam/lather in-use with ease of rinse; they can consist of mixtures of anionic, cationic, amphoteric, and nonionic. Surfactants used in leave-on compositions on the other hand are not required to have such properties. Rather, as leave-on compositions are not intended to be rinsed-off they need to be non-irritating and therefore it would be necessary to minimize the total level of surfactant, and particularly the total level of anionic surfactant in leave-on compositions. Therefore, the preferred leave-on personal care compositions of the present invention contain, with respect to surfactants, predominantly nonionic surfactants. The anionic surfactants are present in an amount of at most 5 wt % on total composition, preferably from 0.01 to 4 wt %, more preferably from 0.01 to 3 wt %, most preferably from 0.01 to 2 wt % and optimally are substantially absent (e.g. less than 1 wt %, preferably less than 0.1 wt %, or even less than 0.01 wt %). Salts of 12-HSA are not considered anionic surfactants herein. The total level of surfactant in the inventive compositions is preferably no more than 10 wt % on total composition, more preferably below 8 wt %, most preferably at most 5 wt %.

A wide variety of packaging can be employed to store and deliver the personal care compositions. Packaging is often dependent upon the type of personal care end-use. For instance, leave-on skin lotions and creams, shampoos, hair conditioners and shower gels generally employ plastic containers with an opening at a dispensing end covered by a closure. Typical closures are screw-caps, non-aerosol pumps and flip-top hinged lids. Packaging for antiperspirants, deodorants and depilatories may involve a container with a roll-on ball on a dispensing end. Alternatively these types of personal care products may be delivered as a stick composition formulation in a container with propel-repel mechanism where the stick moves on a platform towards a dispensing orifice. Metallic cans pressurized by a propellant and having a spray nozzle serve as packaging for antiperspirants, shave creams and other sprayable personal care products. Toilet bars may have packaging constituted by a cellulosic or plastic wrapper or within a cardboard box or even encompassed by a shrink wrap plastic film.

Method for Preparing the Personal Care Composition

It was found that the eutectic mixtures of the invention can be formulated into personal care compositions without losing their eutectic properties, i.e. the lower melting point. This can be achieved by separately making the eutectic mixture and combine this pre-formed eutectic mixture with the other ingredients of the personal care composition.

The invention thus also relates to a method for preparing the personal care composition of the present invention comprising the step of mixing the pre-formed active eutectic mixture of butyl methoxydibenzoylmethane, isopropyl myristate and if present 12-hydroxystearic acid with part or all of the remaining ingredients of the personal care composition.

This results in a product that comprises BMDM and optionally 12-HSA with a lower melting point (as part of the eutectic mixture) but also provides a product that is storage stable in that for example the BMDM and/or 12-HSA does not re-crystallize, or at least at a slower pace and/or only partially. These advantages are absent or at least less pronounced when the 12-HSA is formulated into a personal care composition without BMDM and IPM; when BMDM is formulated into a personal care composition without IPM and optionally 12-HSA; or if the BMDM, IPM and 12-HSA are added as separate ingredients (i.e. not as a pre-formed eutectic mixture).

The invention also concerns the personal care composition of the invention obtainable by the method for preparing the personal care composition.

The invention further concerns a method of applying to human skin the personal care composition of the invention.

The invention is now illustrated by the following non-limiting examples.

EXAMPLES

Melting Point (DSC Curve)

A Mettler DSC 823 was used for the thermal analyses to measure the melting point.

For the "pure" mixtures, i.e. only containing butyl methoxydibenzoylmethane (BMDM), isopropyl myristate (IPM) and 12-hydroxy stearic acid (12-HSA), the temperature range and scanning speed were set to −70 to 100° C. and 2° C./min respectively.

For personal care compositions comprising the eutectic mixture the temperature range and scanning speed were set to 0 to 120° C. and 10° C./min respectively. The measurements were performed with an accuracy of ±0.01° C. The measurements were executed at atmospheric pressure in a dynamic nitrogen atmosphere. The samples were introduced into an aluminum crucible (40 µl) or medium pressure crucible (120 µl). The pan was sealed and introduced at room temperature into the DSC. A special pan, included in the standard accessories of the Mettler equipment, was used to perform the temperature and enthalpy calibration.

Rheological Profile Measurement

MCR 310 rheometer (from Anton Paar Instrument Ltd) was used to study the rheological profile of the samples. This rheometer is connected to a compressed air source to maintain a pressure at 5 bar, which ensures a continuous rotation rate. A plane plate was used having geometry of 25 mm in diameter. An automatic controlled rate mode was used to measure the forces in a shear rate range from 0.01 to 1000 s−1 in a consistent temperature of 25 degrees Celsius.

Samples were transported slowly from the glass vessels to the cell by a spatula in order to avoid an introduction of extra shear forces. Care was taken to fill the cell enough, so no air bubbles were entrained during the measurement.

Example 1

Mixtures of BMDM, IPM and if present 12-HSA where prepared as follows, using the ingredients as in Table 1 and the amounts mentioned in Tables 2A and 2B.

The three components BMDM, IPM and 12-HSA were weighed and then mixed by grinding in a mortar and pestle until a homogenous and transparent mixture was obtained

TABLE 1

Ingredients of ternary eutectic mixtures

| Ingredient | Purity | CAS# | Supplier | Melting Point (° C.) |
|---|---|---|---|---|
| 12-HSA | 95% | 106-14-9 | Alfa Aesar | 81.5 |
| BMDM (Parsol 1789 ®) | 99.5% | 70356-09-1 | DSM | 84.8 |
| IPM | 99% | 110-27-0 | Sigma | 8.9 |

The melting point of these mixtures was measured and the results are shown in Tables 2A and 2B. It is clearly shown that specific mixtures have a lower melting temperature. The lowest measured melting point of about 5.6 degrees Celsius was determined for a eutectic composition of BMDM, IPM and 12-HSA in a weight ratio of 1:9 and a 12-HSA concentration of 3.5 wt % with respect to the total weight of the three components together. This composition is believed to be close to the "true" eutectic composition of this ternary system.

TABLE 2A

Melting point of mixtures of BMDM, IPM and 12-HSA

| The weight ratio of BMDM to IPM | Concentration of 12-HSA (wt %) | | | | | | |
|---|---|---|---|---|---|---|---|
| | 0 | 0.5 | 1 | 2 | 3.5 | 6 | 7 |
| | Melting point of BMDM, IPM and 12-HSA (° C.) | | | | | | |
| 9:1 | 78.3 | 78.2 | 76.8 | — | — | — | — |
| 8:2 | 75 | 74.33 | 73.9 | — | — | — | — |
| 7:3 | 70.4 | 71.4 | 72.6 | — | — | — | — |
| 4:6 | 67 | 67.8 | 70 | — | — | — | — |
| 5:5 | 63 | 60.4 | 65.4 | — | — | — | — |
| 4:6 | 61.5 | 60.6 | 55.8 | — | — | — | — |
| 3:7 | 7.9 | 7.8 | 8.1 | 7.2 | 7 | 8.1 | — |
| 2:8 | 7.9 | 8.1 | 8 | 5.9 | 6.1 | 8.1 | 68.6 |
| 1:9 | 7.9 | 7.9 | 8.1 | 8.3 | 5.6 | 7 | 67.3 |
| 1:10 | 8.4 | 8.0 | 5.7 | 7.9 | 5.9 | — | — |
| 1:15 | 8.5 | 8.5 | 8.2 | 8.1 | 8.1 | 9.5 | — |
| 1:16 | 8.4 | 8.3 | 8.1 | 8.0 | 8.0 | 56.1 | — |

TABLE 2B

Melting point of mixtures of BMDM, IPM and 12-HSA

| The weight ratio of BMDM to IPM | Concentration of 12-HSA (wt %) | | |
|---|---|---|---|
| | 9 | 10 | 20 |
| | Melting point of BMDM, IPM and 12-HSA (° C.) | | |
| 9:1 | — | 77.1 | 80.6 |
| 8:2 | — | 73.2 | 69.1 |
| 7:3 | — | 68.8 | 67.3 |
| 4:6 | — | 60 | 65.6 |
| 5:5 | — | 60 | 64.8 |
| 4:6 | — | 55.8 | 65.3 |
| 3:7 | — | 55.3 | 64.6 |
| 2:8 | 69.2 | 59.4 | 64.2 |
| 1:9 | 70.5 | 58.1 | 64.5 |

Example 2

A personal care composition (A2) according to Table 3A comprising a pre-formed mixture of Butyl Methoxydibenzoylmethane, Isopropyl myristate and 12-hydroxystearic acid was prepared using the following protocol.

1. Phase A was prepared by mixing the ingredients and heating the mixture to 70 degrees Celsius to dissolve the ingredients.
2. Phase B was prepared by mixing sodium polyacrylate and 1,3-butylene glycol and adding them to Phase A. Glycerin was used to flush the beaker and decanted into phase A. The same was repeated with water.
3. Phase C was prepared by mixing the ingredients at 75 degrees Celsius under manual stirring until the phase was transparent.
4. Phase D was prepared by mixing the ingredients of the eutectic mixture (i.e. BMDM, IPM and 12-HSA) in a mortar and pestle until a transparent liquid was obtained. This liquid was added to Phase C.
5. The ingredients of phase E and F were mixed separately and added at 75 degrees Celsius to the mixture obtained after step 4) and stirred manually.
6. Phase G was added to the mixture obtained after step 5) and the mixture was homogenized by mixing for 3 minutes with a Silverson mixer at speed setting 4.
7. The mixture obtained after step 6) was added to the combined phases A+B obtained after step 2). Phase H was used to flush the beaker and completely transfer the mixture from step 6) into the combined phases A+B from step 2). The resulting mixture was homogenized using a Silverson mixer at setting 7 for 10 min until a homogenous mixture is obtained.
8. Sodiumpolyacrylate and 1,3-butylene glycol were mixed and heated to 75 degrees Celsius until dissolved to form phase I. The resulting liquid was added to the main mix from step 7) to increase the viscosity. Water was used to flush the beaker. After phase I had been completely transferred the mixture was homogenized using a Silverson mixer at speed setting 7 for 5 min. The mixture was then stirred until it had cooled down to below 45 Degrees Celsius.
9. The ingredients of phase J were mixed and added to the main mix obtained after step 8) after it had cooled down to below 35 degrees Celsius. The resulting mixture was homogenized for 3 min using a Silverson mixer at speed setting 7.
10. The ingredients of phase K are added to the mixture obtained after step 9 and homogenized for 5 min using a Silverson at speed stetting 7.

TABLE 3A

Personal care composition A2 (wt %)

| Phase | Ingredient | A2 |
|---|---|---|
| A | water | 49.72 |
| | EDTA Na$_2$ | 0.05 |
| | methyl paraben | 0.20 |
| | sodium hydrogen N-(1-oxooctadecyl)-L-glutamate | 0.50 |
| B | Sodium Polyacrylate | 0.35 |
| | 1,3-butylene glycol | 1.00 |
| | glycerin (Flush) | 3.00 |
| | water | 2.00 |
| C | propyl paraben | 0.10 |
| | stearyl heptanoate | — |
| | cetearyl alcohol | 2.4 |
| | dicaprylyl carbonate | — |
| | Hydrogenated Polydecene (Puresyn 6, ex ExxonMobile) | — |
| D | Butyl Methoxydibenzoylmethane (Parsol 1789, ex DSM) | 0.97 |
| | Isopropyl myristate (ex Kunshan Daily Chem) | 8.69 |
| | 12-hydroxystearic acid (ex Biotor) | 0.35 |
| E | sucrose polystearate (Emulgade SUCRO, ex Cognis) | 1.00 |
| | DC 200/200 cst | 2.00 |
| F | Butyl Methoxydibenzoylmethane (Parsol 1789, ex DSM) | — |
| | Ethylhexyl Methoxycinnamate (Parsol MCX, ex DSM) | 6.00 |
| G | Titanium Dioxide (SA-TR-10, ex Miyoshi Kasei) | 0.60 |
| H | Capric Triglycerides) GTCC (Flush), myritol 318; ex Croda) | 2.00 |
| I | sodium polyacrylate (Covacryl MV 60, ex Sensient) | 0.20 |
| | 1,3-butylene glycol | 1.00 |
| | water | 2.00 |
| J | water | 12.00 |
| | vitamin B3 | 3.00 |
| K | Annmonium Lactate (L) (70%) | 0.071 |
| | Jasmin silk 3457M | 0.40 |
| | Phenoxyethanol | 0.40 |

Example 3

Personal care compositions according to Table 3B comprising were prepared using the following protocol. In A1, butyl methoxydibenzoylmethane, isopropyl myristate and 12-hydroxystearic acid were added separately (i.e. not added as a pre-formed eutectic mixture). A3 comprises butyl methoxydibenzoylmethane and 12-hydroxystearic acid but no isopropyl myristate.

1. Phase A was prepared by mixing the ingredients and heating the mixture to 70 degrees Celsius to dissolve the ingredients.
2. Phase B was prepared by mixing sodium polyacrylate and 1,3-butylene glycol and adding them to Phase A. Glycerine was used to flush the beaker and decanted into phase A. The same was repeated with water.
3. Phase C was prepared by was prepared by mixing the ingredients at 75 degrees Celsius under manual stirring until the phase was transparent. For A1, 12-HSA and isopropyl myristate were added to the dispersion one by one as the last ingredients. In A3 12-HSA was added to the dispersion as the last ingredient, this phase does not contain isopropyl myristate.
4. The ingredients of phase D and E were mixed separately and then added to the mixture obtained in step 3).
5. Phase F was then added to the mixture obtained after step 4) and the resulting dispersion was homogenized using a Silverson mixer at speed setting 4.
6. The mixture obtained after step 5) was then added to the combined phases A and B obtained after step 2). Phase G was used to flush the beaker and completely transfer the mixture from step 5) into the combined phases A and B from step 2). The resulting mixture was homogenized using a Silverson mixer at setting 7 for 10 min until a homogenous mixture is obtained.
7. Sodium polyacrylate 1,3-butylene glycol were mixed and heated to 75 degrees Celsius until dissolved to form phase H. The resulting liquid was added into the main mix from step 6) to increase the viscosity. Water was used to flush the beaker. After phase H had been completely transferred the mixture was homogenized using a Silverson mixer at speed setting 7 for 5 min. The mixture was then stirred until it had cooled down to below 45 degrees Celsius.
8. The ingredients of phase I were mixed and added to the main mix obtained after step 7) after it had cooled down to below 35 degrees Celsius. The resulting mixture was homogenized for 3 min using a Silverson mixer at speed setting 7.
9. The ingredients of phase J were added to the mixture obtained after step 8 and homogenized for 5 min using a Silverson at speed stetting 7.

TABLE 3B

Personal care composition A1 and A3 (wt %)

| Phase | Ingredient | A1 | A3 |
|---|---|---|---|
| A | water | 49.72 | 41.72 |
|  | EDTA Na$_2$ | 0.05 | 0.05 |
|  | methyl paraben | 0.20 | 0.20 |
|  | sodium hydrogen N-(1-oxooctadecyl)-L-glutamate | 0.50 | 0.50 |
| B | Sodium Polyacrylate | 0.35 | 0.35 |
|  | 1,3-butylene glycol | 1.00 | 1.00 |
|  | glycerin (Flush) | 3.00 | 3.00 |
|  | water | 2.00 | 2.00 |
| C | propyl paraben | 0.10 | 0.10 |
|  | stearyl heptanoate | — | 1.00 |
|  | cetearyl alcohol | 2.4 | 2.40 |
|  | dicaprylyl carbonate | — | 4.00 |
|  | Hydrogenated Polydecene (Puresyn 6, ex ExxonMobile) | — | 3.00 |

TABLE 3B-continued

Personal care composition A1 and A3 (wt %)

| Phase | Ingredient | A1 | A3 |
|---|---|---|---|
|  | Butyl Methoxydibenzoylmethane (Parsol 1789, ex DSM) | — | — |
|  | Isopropyl myristate (ex Kunshan Daily Chem) | 8.69 | — |
|  | 12-hydroxystearic acid (ex Biotor) | 0.35 | 0.35 |
| D | sucrose polystearate (Emulgade SUCRO, ex Cognis) DC 200/200 cst | 1.00 2.00 | 1.00 2.00 |
| E | Butyl Methoxydibenzoylmethane (Parsol 1789, ex DSM) | 0.97 | 0.97 |
|  | Ethylhexyl Methoxycinnamate (Parsol MCX, ex DSM) | 6.00 | 6.00 |
| F | Titanium Dioxide (SA-TR-10, ex Miyoshi Kasei) | 0.60 | 0.60 |
| G | Capric Triglycerides) GTCC (Flush), myritol 318; ex Croda) | 2.00 | 2.00 |
| H | sodium polyacrylate (Covacryl MV 60, ex Sensient) | 0.20 | 0.20 |
|  | 1,3-butylene glycol | 1.00 | 1.00 |
|  | water | 2.00 | 2.00 |
| I | water | 12.00 | 12.00 |
|  | vitamin B3 | 3.00 | 3.00 |
| J | Annmonium Lactate (L) (70%) | 0.071 | 0.071 |
|  | Jasmin silk 3457M | 0.40 | 0.40 |
|  | Phenoxyethanol | 0.40 | 0.40 |

Results

The stability of the personal care compositions A1 to A3 was measured for fresh compositions and composition stored for a month at 50 degrees Celsius using DSC (results in FIGS. 1 to 3) and rheological profile measurement (results in FIGS. 4 and 5) as described above.

Figure 1:
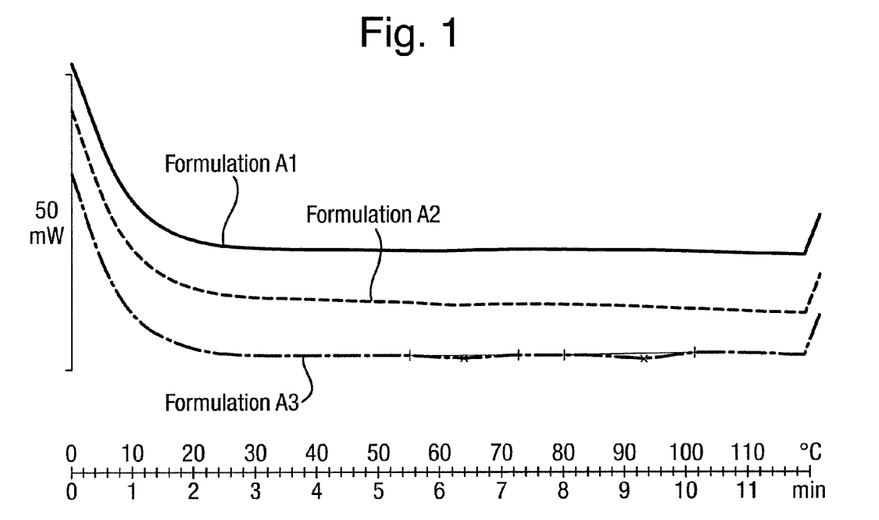
FIG. 1 shows DSC curves demonstrating the thermal stability behavior of a fresh composition containing 12-HSA, BMDM and IPM added separately (A1—top curve), a fresh composition comprising 12-HSA, BMDM and IPM mixed first and then added (A2—middle curve) and a fresh composition without IPM (A3—bottom curve)

FIG. 1 shows that for the fresh compositions there is no crystallization for A1 (all three components, but added separately) and A2 (all three components mixed first and then added). Composition A3 (only 12-HSA and BMDM) shows two crystallization events at high temperature.

Figure 2:
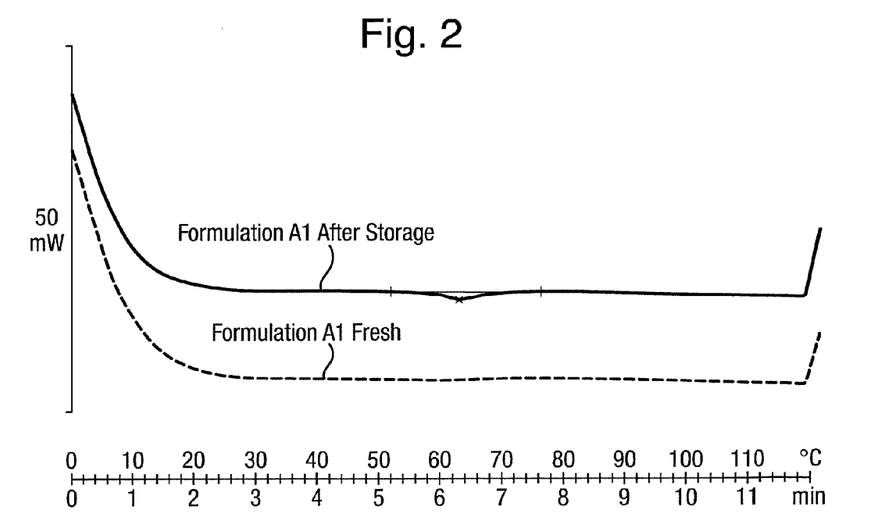
FIG. 2 shows DSC curves demonstrating the thermal stability behavior of the formulation A1 of FIG. 1 wherein the bottom curve is for the fresh formulation and the top curve is after 1 month stability test at 50° C. plus storage at room temperature for 1 month.

FIG. 2 shows that for the fresh A1 composition there is no crystallization, but that for A1 after storage for 1 month at 50 degrees Celsius there is one crystallization peak (likely to be 12-HSA).

Figure 3:
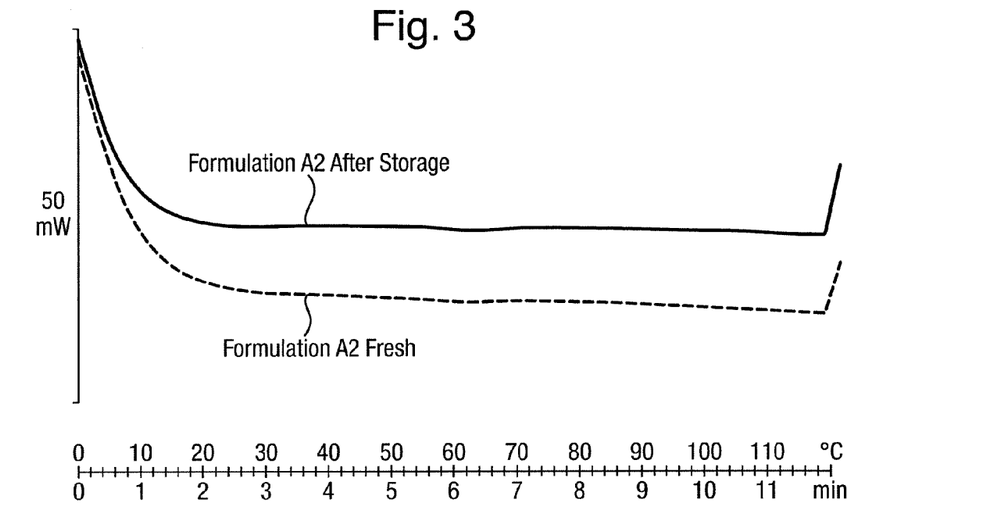
FIG. 3 shows DSC curves demonstrating the thermal stability behavior of the formulation A2 of FIG. 1 wherein the bottom curve is for the fresh formulation and the top curve is after 1 month stability test at 50° C. plus storage at room temperature for 1 month.

FIG. 3 shows that for fresh and stored samples of A2 (according to the invention) no crystallization was detected.

Figure 4:
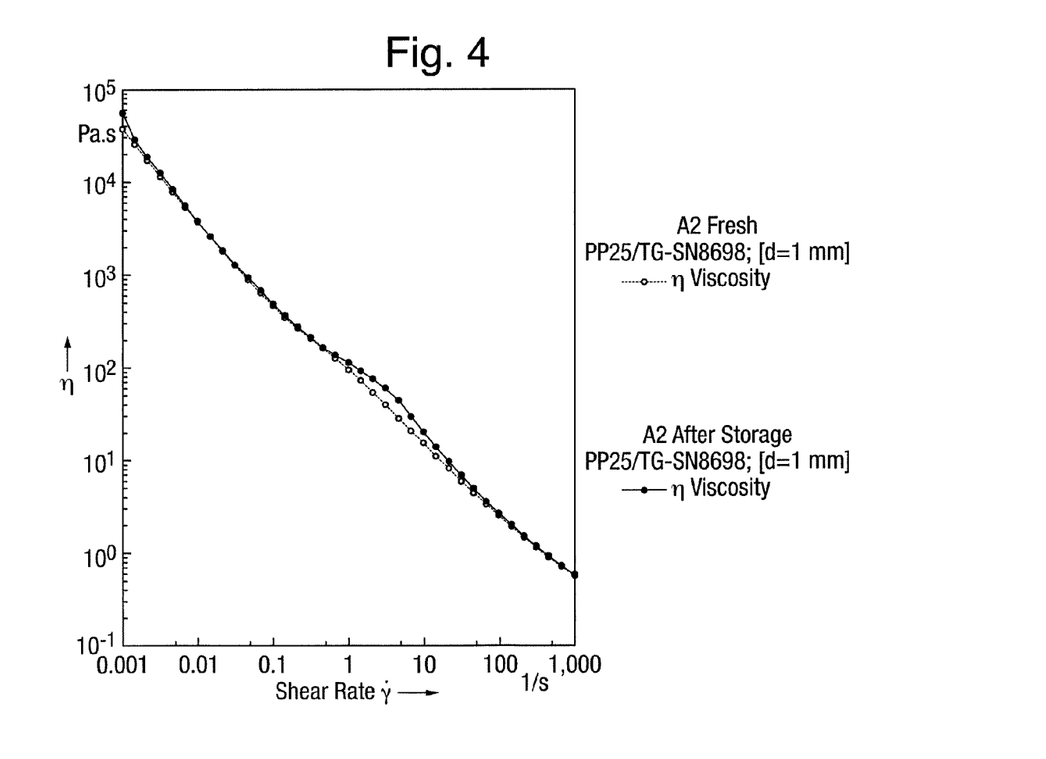
FIG. 4 shows viscosity vs shear rate behavior at 25° C. of the formulation A2 of FIG. 1 wherein the bottom curve is for the fresh formulation and the top curve is after 1 month stability test at 50° C.

FIG. 4 indicates that the rheological profile (i.e. viscosity) measured at different shear rates for a freshly assembled sample A2 and sample A2 stored for 1 month at 50 degrees Celsius is essentially the same. This demonstrates that for formulations according to the present invention, where the eutectic components have been pre-formed before adding them to the composition, will show no deterioration of the texture upon storage.

Figure 5:
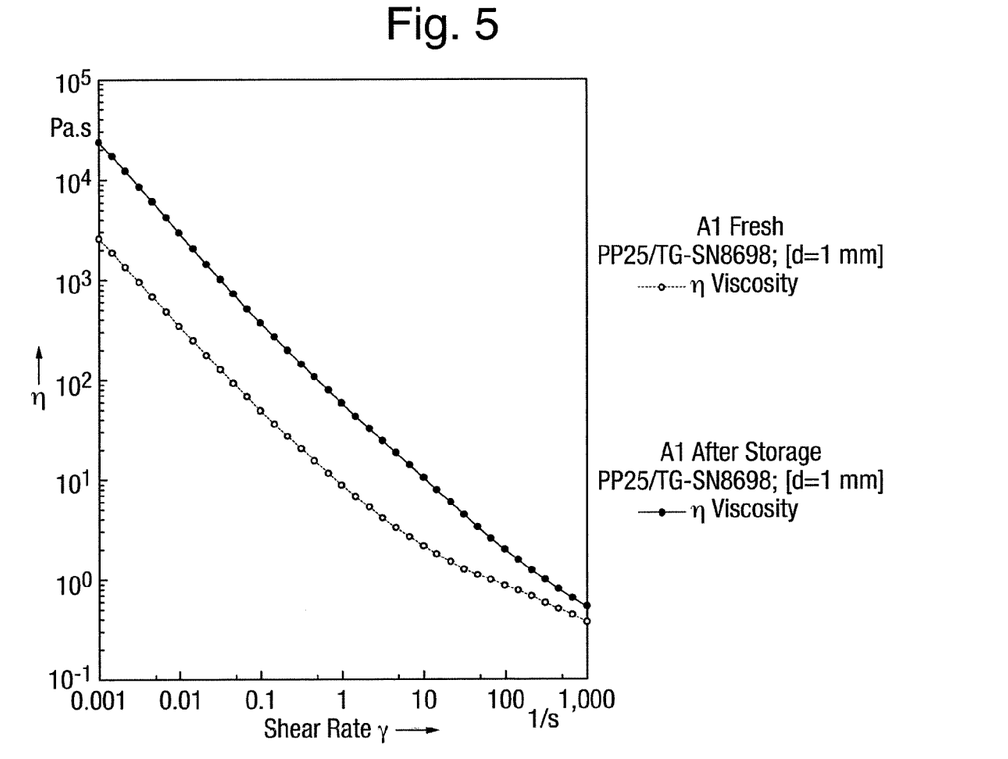
FIG. 5 shows viscosity vs shear rate behavior at 25° C. of the formulation A1 of FIG. 1 wherein the bottom curve is for the fresh formulation and the top curve is after 1 month stability test at 50° C.

FIG. 5 indicates that the viscosity measured at different shear rates for a freshly assembled sample A1 and sample A1 stored for 1 month at 50 degrees Celsius is significantly different. The stored sample shows a significantly higher viscosity. This demonstrates that for formulations where the eutectic components have not been pre-formed before adding them to the composition, but added separately, the texture will markedly change (deteriorate) during storage.

The invention claimed is:

1. An active eutectic mixture of butyl methoxydibenzoylmethane, and isopropyl myristate wherein the weight ratio of butyl methoxydibenzoylmethane to isopropyl myristate is from 3:7 to 1:15 and wherein the eutectic mixture has a melting point below 15 degrees Celsius, and further wherein the mixture comprises 12-hydroxystearic acid in an amount from 0.5 to 6 wt % by total weight of the mixture and where 0.1 to 60% by weight of the eutectic mixture is suitable for use in a personal care composition.

2. The mixture according to claim 1 wherein the weight ratio of butyl methoxydibenzoylmethane to isopropyl myristate is from 3:7 to 1:10.

3. The mixture according to claim 1 wherein the mixture has a melting point below 12 degrees Celsius.

4. A personal care composition comprising
 i) the active eutectic mixture according to claim 1, and
 ii) a cosmetically acceptable carrier.

5. The composition according to claim 4 comprising 5 to 15 wt % of the eutectic mixture calculated on total personal care composition.

6. The composition according to claim 4 comprising from 0.1 to 8 wt % of butyl methoxydibenzoylmethane.

7. The composition according to claim 4 comprising from 0.1 to 10 wt % of butyl methoxydibenzoylmethane.

8. The composition according to claim 4 further comprising additional sunscreen agents, selected from organic UVA sunscreen, organic UVB sunscreen, inorganic sunscreen and combinations thereof.

9. The composition according to claim 4 further comprising a vitamin and the composition has a viscosity from 1 to 500 Pas at 20° C.

10. The composition according to claim 4 which is selected from leave-on skin lotions and creams, shampoos, hair conditioners, shower gels, toilette bars, antiperspirants, deodorants, shave creams, lipsticks, foundations and sunscreen lotions.

11. The composition according to claim 4 wherein the composition is a sunscreen composition or a leave-on skin lotion or cream.

12. A method for preparing a personal care composition according to claim 4 comprising the step of mixing the pre-formed active eutectic mixture of butyl methoxydibenzoylmethane, isopropyl myristate and 12-hydroxystearic acid with additional agents of a personal care composition.

13. A method of treating human skin comprising the step of applying the personal care composition according to claim 4 to the skin.

* * * * *